United States Patent [19]
Nomura

[11] Patent Number: 6,022,602
[45] Date of Patent: *Feb. 8, 2000

[54] PLASMA MODIFICATION OF LUMEN SURFACE OF TUBING

[75] Inventor: Hiroshi Nomura, Shorewood, Minn.

[73] Assignee: NeoMecs Incorporated, St. Louis Park, Minn.

[*] Notice: This patent is subject to a terminal disclaimer.

[21] Appl. No.: 08/313,416

[22] Filed: Sep. 27, 1994

Related U.S. Application Data

[63] Continuation-in-part of application No. 08/187,177, Jan. 26, 1994, abandoned.

[51] Int. Cl.[7] .............................. A61M 29/02; B32B 3/10
[52] U.S. Cl. ................. 428/36.8; 428/36.91; 428/131; 428/134; 428/336; 623/12; 604/96; 427/2.12; 427/256; 427/489; 427/490
[58] Field of Search ................. 428/36.8, 36.9, 428/36.91, 131, 134, 137, 332, 336; 623/1, 12, 11; 427/2.1, 2.12, 256, 261, 489, 490, 491; 604/96

[56] References Cited

U.S. PATENT DOCUMENTS

| | | | |
|---|---|---|---|
| 4,349,582 | 9/1982 | Beerwald et al. | 427/575 |
| 4,656,083 | 4/1987 | Hoffman et al. | 442/123 |
| 4,687,482 | 8/1987 | Hanson | 623/1 |
| 4,690,844 | 9/1987 | Saudagar | 428/36.8 |
| 4,692,347 | 9/1987 | Yasuda | 427/491 |
| 4,718,907 | 1/1988 | Karwoski et al. | 623/12 |
| 4,844,986 | 7/1989 | Karakelle et al. | 428/447 |
| 4,948,628 | 8/1990 | Montgomery et al. | 427/570 |
| 4,980,231 | 12/1990 | Baker et al. | 428/36.9 |
| 5,034,265 | 7/1991 | Hoffman et al. | 442/126 |
| 5,132,108 | 7/1992 | Narayanan et al. | 424/78.17 |
| 5,244,654 | 9/1993 | Narayanan et al. | 424/78.17 |
| 5,254,372 | 10/1993 | Nichols | 427/488 |

FOREIGN PATENT DOCUMENTS

3116026  10/1982  Germany.

*Primary Examiner*—Rena Dye
*Attorney, Agent, or Firm*—Robert J. Petersen

[57] ABSTRACT

The lumen surface of tubing is modified by exposure to a gas plasma in a vacuum apparatus. A method and apparatus are disclosed whereby plasma treatment of the lumen surface, such as by deposition of a plasma polymerizate, may be achieved inside a continuous length of tubing. A gas such as a monomer vapor is caused to enter the lumen of the tubing through openings sequentially arranged at a periodic interval along the length of the tubing, and is excited to a plasma state concurrently as the tubing passes through a tubular reaction conduit having an inner diameter in occlusive contact with the tubing's outer diameter. Essentially crack-free plasma polymerizate coatings with thicknesses greater than 1000 angstroms are selectively deposited on the lumen wall of the continuous tubing. Plasma-modified tubing is prepared having usefulness in medical devices such as catheters, vascular grafts and enteral feeding tubes.

15 Claims, 4 Drawing Sheets

PLASMA MODIFICATION OF LUMEN SURFACE OF TUBING

This application is a continuation-in-part of application Ser. No. 08/187,177, filed Jan. 26, 1994, now abandoned.

FIELD OF THE INVENTION

The invention relates to the treatment of an article with a gas plasma, more specifically to a method and apparatus for modifying the lumen surface of a continuous length of a dielectric tubing by gas plasma treatment, and to articles made thereby.

BACKGROUND OF THE INVENTION

For many uses, particularly in the area of biomaterials for medical applications, it is beneficial to modify the internal surfaces of tubing made of dielectric materials. This must ordinarily be accomplished in a procedure that occurs after the tubing itself has been manufactured. Treatment of a surface with a gas plasma is a versatile method for modifying the surface of a solid material. A major advantage of this approach is the capability of applying very thin, highly adherent, uniform coatings free of pinholes, without changing the composition and physical characteristics of the underlying material being coated. This can be achieved by means of a gas plasma that employs a polymerizing monomer or mixture of such monomers. Alternatively, gas plasmas may also be used to clean and crosslink naturally occurring surfaces of materials while not depositing polymerizates, such as by treatment with plasmas from gaseous compositions that do not contain polymerizing monomers. It is nevertheless a major obstacle to introduce a reactive gas or gas mixture into the lumen of a continuous length of tubing that is not itself naturally porous along its length. Even materials assumed to be naturally porous to some extent may not be amenable to treatment of their lumen surfaces with a gas plasma, if the treatment is to be accomplished in the context of a continuous process operating on a continuous length of material. For instance, gas plasma treatment of the inner surface of vascular grafts has heretofore been essentially limited to the processing of short lengths. The walls of vascular grafts, while thin and flexible, are surprisingly tight, such that a pressure difference of as little as one torr between the outside and inside of the vascular graft under the vacuum conditions employed in gas plasma treatment is sufficient to collapse the graft. Thus, many types of vascular grafts cannot be plasma-treated on their lumen surfaces in a continuous process operating on continuous lengths.

Efforts have been made by others to treat lumen surfaces of some types of tubing by means of gas plasmas. U.S. Pat. No. 4,632,842 discloses a method of coating the surfaces and pores of a porous tubular substrate with a polymerizing gas plasma to generate a material useful as a vascular graft. U.S. Pat. No. 4,687,482 discloses a vascular prosthesis having a hydrophobic polymeric layer deposited on its lumen surface such as by gas plasma treatment. U.S. Pat. No. 5,034,265 discloses a method of coating a woven or knit vascular prosthesis with a gas plasma by which a fluorinated hydrocarbon monomer is grafted to its surface. U.S. Pat. No. 5,244,654 discloses a method to treat the internal surface of a silicone rubber tube of short length with an oxidizing gas plasma to prepare a surface for subsequent derivatization with biocompatibility enhancing agents. U.S. Pat. No. 4,948,628 discloses an apparatus and method for treating the lumen surface of a small diameter tube by drawing a long length of it through a bore in a two-chamber housing having a gas pressure differential between the two chambers, delivering radiofrequency power to gases in the tube lumen while it is within the bore. U.S. Pat. No. 4,692,347 discloses a method of selectively coating the lumen surface of a long length of tubing by introducing a reactive gas at one end of its length, removing residual or unreacted gas from the other end by vacuum (which establishes a flow of gas through the lumen), and passing the tubing through a radiofrequency field wherein the gas mixture flowing in its lumen is excited to a plasma state. This latter method was capable of selectively coating the lumen surface of lengths of tubing as long as 10 to 15 meters.

None of these patents specifically disclose methods and apparatus for plasma-treating the lumen walls of continuous length tubing. In this respect, the above approaches appear to lack a key element for widespread commercial utility. The latter two disclosures indicate that long lengths may be plasma-treated within the tubing lumen. Nevertheless, they do not appear to provide a necessary control of monomer pressure and flow rate to achieve uniform plasma polymerizate coatings on tubing lumen surfaces.

A pressure drop occurs when gas flows through a lumen of a tube, and the magnitude of this pressure drop restricts the length of the tube that can be properly treated. In U.S. Pat. No. 4,692,347, silicone rubber tubing was used that had an internal diameter of 3.3 mm. From an M.S. thesis by Y. Matsuzawa, *Continuous Plasma Polymerization for Preparation of Composite Reverse Osmosis Hollow Fiber Membranes and of Biomedical Plastic Tubing* (see p. 64, FIG. 27), tubing such as this was found to have a pressure drop in excess of 700 mtorr per meter at an argon gas feed rate of 0.104 sccm (standard cubic centimeters per minute). Because of this pressure drop, the pressure of a reactive gas in the lumen must unfortunately be quite nonuniform along its length. For a polymerizing monomer, the nonuniform gas pressure leads to nonuniform deposition rates of plasma polymerizate on lumen walls along the length of the tubing lumen. Similarly, crosslinking or other surface modifications of lumen surfaces by nonpolymerizing gas plasmas will be nonuniform along the tubing length. Furthermore, some gases readily permeate through the walls of certain materials such as silicone rubber, such that the pressure of monomer vapor inside the lumen cannot be maintained in an optimum range when the outside of the tube is under a vacuum. In the specific case of silicone rubber, efforts to apply plasma coatings from silane or siloxane gaseous monomers following the approach of U.S. Pat. No. 4,692,347 will generally fail because of monomer losses through the tubing wall, and no such examples are given in that patent's description.

The need remains for an approach that can internally coat or modify the lumen surface of a tubing wherein the tubing is continuous, i.e., not limited to 10 meters, 15 meters, or even 100 meters in treatable length. Further, the need remains for a method that can treat the lumen surfaces of thin-walled tubing such as vascular grafts wherein the wall porosity is so low that minor pressure differences are sufficient to collapse the tubing in a gas plasma treatment operation. Further, a need exists for a method whereby nonporous or nearly nonporous tubing can be continuously coated in a commercially attractive manner that does not limit the length of the material to be processed. In addition, a need exists whereby the monomer feed rate to a polymerizing plasma zone can be controlled to a narrow range so as to lay down an essentially uniform thickness of plasma polymerizate on lumen surfaces.

According to Yasuda (U.S. Pat. No. 4,692,347), the energy input per unit mass of monomer is a significant parameter in determining the character of the polymeric coating obtained in a plasma polymerization. Thus, for example, where W=power input in watts
F=monomer flow rate in moles per second
M=molecular weight of the monomer a tight amorphous polymeric layer effective as a barrier layer was obtained by Yasuda where W/FM was equal to $10^9$ to $10^{10}$ Joules per kilogram (J/kg). A relatively permeable coating was obtained where W/FM was equal to $10^7$ to $10^8$/kg. Thicknesses in the range of 100 to 500 angstroms were preferred. At thicknesses significantly greater than 1000 Å, the coatings had a tendency to suffer from stress cracking. By way of example, fluoropolymer coatings deposited from a glow discharge plasma of tetrafluoroethylene have been noted by Matzuwara (loc. cit.) to show cracks when the flow rate of the monomer was increased beyond the range of 0.115–0.331 $cm^3$ (STP)/min in a glow discharge polymerization operated in the range of 6–14 watts in silicone rubber tubing at a residence time of 3–20 seconds. For many purposes, a barrier layer 100–500 Å thick deposited by plasma polymerization on the lumen of a tubing is inadequate. The surface roughness of the lumen of a tubing may be too large to be adequately protected or sealed by such a thin deposit of plasma polymerizate. As an example, elastomeric tubing filled with an opacifying pigment, such as titanium dioxide in a white silicone rubber tubing, will tend to have a surface made rougher by the presence of pigment particles in the surface layer. Additionally, barrier layers deposited on the tubing lumen surfaces ideally should be able to withstand the insertion of connectors into the tubing without significant loss of integrity. Thicker barrier layers are needed, possessing thereby sufficient abrasion resistance to safely accommodate insertion of connectors. Such thicknesses do not appear possible within the confines of the method disclosed by Yasuda because of stress cracking.

An object of the invention therefore is to modify the lumen surface of a continuous length of nonporous or sparingly porous tubing by a gas plasma. By "continuous length" is meant a span of tubing up to kilometers in reach, that is not limited in extent by reason of accessibility of its lumen to reactive gas or gas mixture and establishment of a suitable gas flow for gas plasma development therein. Thus, the tubing may be limited in length to a kilometer or fraction thereof by reason of physical constraints of a plasma apparatus but not by reason of the method of the invention.

Another object of the invention is to modify the lumen surface of a continuous length of the tubing by deposition of a gas plasma polymerizate on the lumen wall out of a polymerizing gas plasma.

Another object of the invention is to deposit plasma polymerizate coatings on the lumen wall of the tubing wherein the coating thickness can be well in excess of 1000 Å while being essentially free of stress cracking.

Another object of the invention is to supply monomer at a narrow range of feed rate to the plasma zone in a tubing lumen throughout the duration of movement of a continuous length of tubing through the plasma treatment zone.

Another object of the invention is to selectively modify the lumen surface of a continuous length of the tubing by a gas plasma, wherewith the external surface of the tubing remains essentially unmodified.

An additional object of the invention is to modify the lumen surface of a continuous length of tubing intended for medical applications such as for catheters, vascular grafts and feeding tubes.

Additional objects, advantages and novel features of the invention will be set forth in the description of the invention which follows, and in part will become apparent to those skilled in the art upon review of the following description or as may be learned through practice of the invention.

SUMMARY OF THE INVENTION

In accordance with the present invention, a method and apparatus have now been developed whereby continuous lengths of nonporous or low-porosity tubing can be treated on their lumen surfaces with a gas plasma to modify or coat those surfaces, and articles useful in medical devices have been made thereby.

The method comprises conveying a continuous length of a tubing through a tubular reaction chamber wherein a radiofrequency field excites a gas or gas mixture to a gas plasma state, the continuous length of tubing having sequentially arranged at a periodic interval along its length openings for communication of a gas between its interior (i.e., its lumen) and its exterior. The tubular reaction chamber, more precisely defined as a conduit, is sized so as to have an internal diameter or a portion of its internal diameter equal to, or only slightly larger than, the external diameter of the tubing to be treated, thereby providing an occlusive contact with the tubing that diverts at least a majority, if not all, of the flow of the gas through the conduit to a pathway via the tubing lumen. The flow of the gas or gas mixture through the tubing lumen is in the direction from a feed source adjacent to one end of the conduit toward a vacuum source adjacent to the other end of the conduit. A pressure differential established and maintained across the length of the conduit causes the gas to flow through the lumen of the tubing, entering and exiting the tubing lumen through the periodically spaced openings along the length of the tubing. Any annular space present between the internal surface of the tubular reaction conduit and the external surface of the tubing in the region of the radiofrequency field is preferably so narrow as to inhibit the development of a glow discharge gas plasma in the annulus under conditions normally suitable for development of a glow discharge gas plasma in the tubing lumen. The gas or gas mixture from which the plasma is to be generated is introduced through an inlet into a vacuum chamber adjoining one end of the conduit, wherein the gas is initially in contact with the external surface of the tubing. Gas flowing into the tubing's lumen and not fully consumed in the glow discharge treatment process is subsequently removed through an outlet to a vacuum source, this outlet being located exteriorly to the tubing in a vacuum chamber adjoining the opposite open end of the tubular reaction conduit relative to the gas inlet chamber.

The apparatus in its preferred form is a vacuum apparatus having two vacuum chambers connected together by one or more tubular reaction conduits. Gas present in either vacuum chamber would be in fluid communication with gas in the other vacuum chamber through the tubular reaction conduit or conduits connecting them. One vacuum chamber has positioned within it one or more dispensers for supplying continuous lengths of tubing. Guides and rollers convey the tubing into one or more tubular reaction conduits at one end, and therefrom at the other end onto one or more receivers located in the other vacuum chamber for taking up the plasma-treated product. For most types of tubing, both the dispensers and the receivers would typically be spools on which tubing would be wound. A drive mechanism causes the tubing to be drawn through the conduits. Either or optionally both vacuum chambers are fitted with outlets to a vacuum source to remove gases, and with pressure monitors.

At least one vacuum chamber is fitted with a gas inlet to supply gas to the glow discharge zone. Pressure monitors are fitted to either or both vacuum chambers. A throttle is positioned in the outlet to the vacuum source. One pressure monitor is connected to a controller for controlling the throttle so as to control system pressure and the magnitude of the pressure differential generated across the tubular reaction conduits. Each tubular reaction conduit itself will typically be a hollow dielectric material transparent to radiofrequency waves, and optimally transparent to visible light as well. The inside surface of the tubular reaction conduit is optionally treated with a polymeric material to reduce frictional resistance to sliding contact movement of a tubing through it. A radiofrequency transmitting electrode, with or without a ground electrode, is mounted externally to the tubular reaction conduit or conduits, whereby a localized radiofrequency field may be generated and a glow discharge developed through a gas.

In accordance with the invention, articles made by this method and associated apparatus include continuous lengths of flexible tubing having perforations periodically spaced along their length and having the lumen surfaces therein modified by plasma treatment uniformly along their length dimension. Alternatively, such articles may consist of continuous linear assemblies of pre-cut sections of flexible tubing connected end-to-end, with periodically spaced openings therein, and having the lumen surfaces therein modified by plasma treatment uniformly along the length of the continuous assembly. Furthermore, medical devices incorporating sections cut from these continuous lengths or assemblies are to be considered as a part of the invention. A particular example of an article of the invention constitutes a flexible, rubbery tubing having an adherent layer of plasma polymerizate of tetrafluoroethylene deposited selectively and uniformly on its lumen surfaces at a thickness well exceeding 1000 Å, this layer being essentially free of cracks. An example of a class of a medical devices advantageously incorporating sections of this tubing includes transcutaneous catheters or enteral feeding tubes.

An advantage of this invention, therefore, is its capability to treat inner surfaces of nonporous or low-porosity tubing in continuous lengths or continuous linear assemblies in a continuous, non-interrupted manner.

A further advantage of this invention is its capability to modify the lumen surfaces of continuous lengths of nonporous or low-porosity tubing such that the deposition rates of a plasma polymerizate, for example, can be essentially the same at an end section of the length of the tubing as would be achieved at a beginning section of the length of the tubing irrespective of its length.

Another advantage of this invention is the capability to control the flow rate of polymerizing monomer to the plasma zone at higher absolute flows so as achieve deposition rates of plasma polymerizate that are both high and essentially uniform along the length of the tubing.

An even further advantage of this invention is its ability to selectively treat the lumen surface of the tubing while not necessarily modifying the outer surface of the same tubing by any significant exposure of the latter to the gas plasma, via control of the annular space dimensions to preclude glow discharge development therein, even though gas feeding the gas plasma is admitted to the apparatus externally to the tubing.

It is also an advantage of the method and apparatus of this invention to be able to simultaneously treat lumen surfaces of a plurality of tubing lines in parallel operation, even when the tubing feedstocks are of different compositions and different diameters.

The practice of this invention will desirably result in continuous lengths of nonporous or low-porosity tubing having its lumen surface modified by a gas plasma uniformly along its length, albeit the tubing will have openings sequentially arranged at a periodic interval along its length. For surprisingly many purposes, the presence of the openings is not detrimental to the usefulness of the treated tubing. Many such uses already involve discrete lengths of tubing. This is particularly true for biomedical devices such as, for example, vascular grafts, catheters or feeding tubes. Openings in a continuous length of tubing can be periodically spaced so as to correspond to the ends of the desired sections of the vascular grafts, catheters or feeding tubes to be cut therefrom, thus allowing essentially full use of the tubing between the openings. In particular, for vascular grafts which are typically used in the form of quite short sections, many such sections may feasibly be cut from each length extending between the periodically spaced openings. For other uses requiring lengths longer than the optimum spacing of openings, means may optionally be employed for sealing off such openings.

Additional features of this invention and the resulting attributes and advantages derived therefrom will become evident to those skilled in the art from examination of the description to follow.

DETAILED DESCRIPTION OF THE INVENTION

Figure 1:
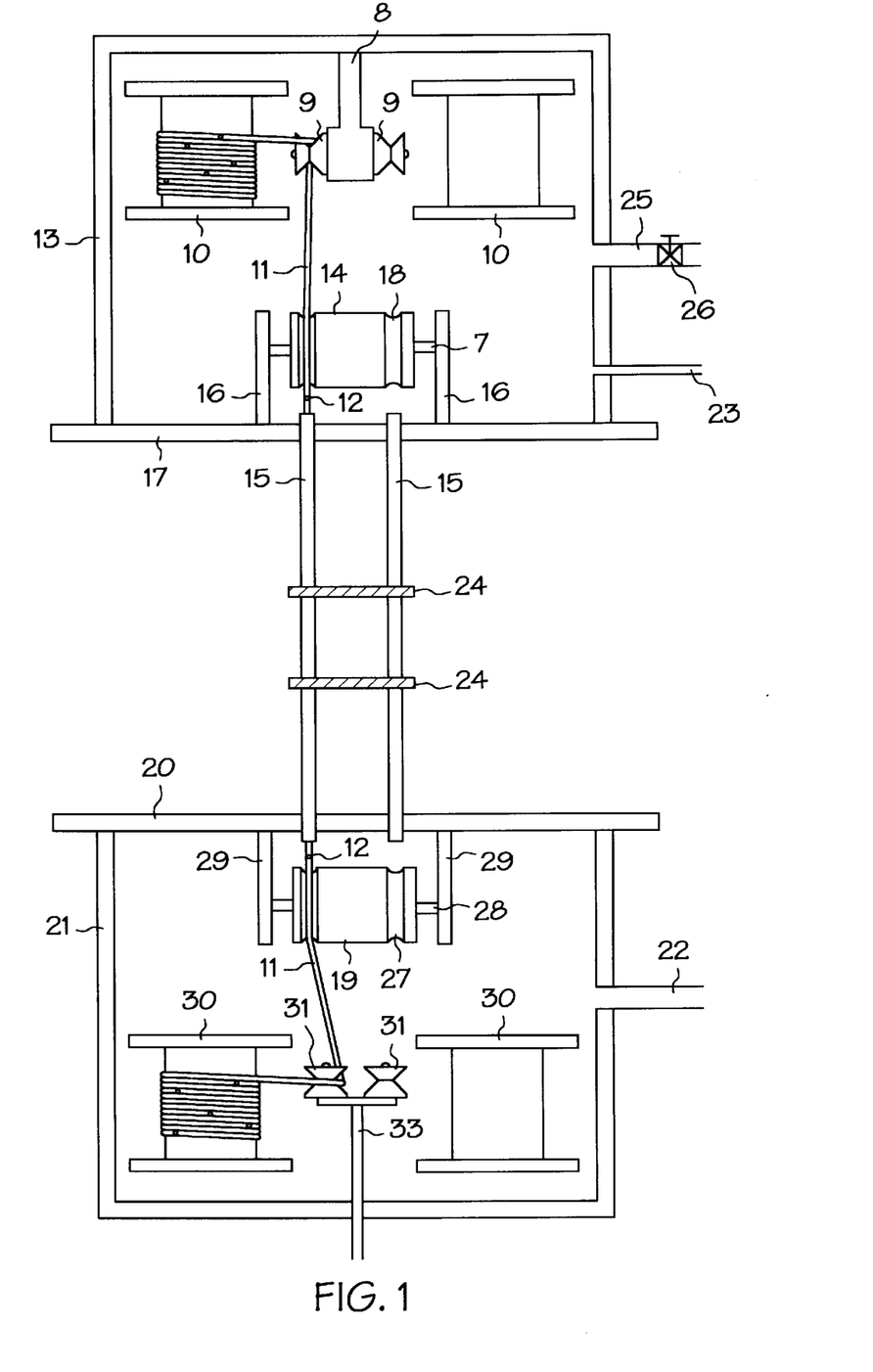
FIG. 1 is a schematic view of an apparatus whereby gas plasma treatment of the lumen of a continuous length of tubing may be accomplished.

FIG. 1 illustrates in an overall manner an apparatus and method of practicing the invention. In this figure, an apparatus is depicted wherein two parallel tubular reaction conduits are provided, although for the sake of added clarity in illustration only one of the tubular reaction conduits and associated equipment for handling the tubing are shown in use. A tubing dispenser such as a supply spool 10 (one of a pair depicted in this figure) containing a continuous length of a tubing 11 having openings 12 periodically distributed along its length is mounted and located within a first vacuum chamber 13. The tubing 11 is fed from the spool 10 and passes over a take-off idler roller 9 onto an aligning guide 14 located at the entrance to a tubular reaction conduit 15. The take-off idler roller 9 may be conveniently mounted to a wall of the first evacuated chamber 13 by means of a mounting block 8. The aligning guide may be secured in place by means of mounting posts 16 fixed to a base plate 17 of the first evacuated chamber 13, the aligning guide having a rotatable shaft 7 communicating with the mounting posts 16. The aligning guide 14 can be essentially an idler roller having one or more grooves 18 in its surface, the grooves 18 positioning one or more lines of tubing 11 for entry into the open end of one or more tubular reaction conduits 15. A tubing 11 to be plasma-treated passes into the tubular reaction conduit 15, wherein a zone of gas plasma is activated within the lumen of the tubing 11. The treated tubing passes through the tubular reaction conduit 15, and travels over a second aligning guide 19 having positioning grooves 27 and mounted to a base plate 20 of a second vacuum chamber 21 by means of a rotatable shaft 28 and shaft mounting posts 29. From thence, the tubing 11 goes onto a lay-on idler roller 31 that guides the tubing onto a receiver such as a product spool 30 positioned in the second vacuum chamber 21. The lay-on idler roller 31 is preferably mounted onto a movable mounting 33 that can be mechanically raised or lowered such as to guide the tubing 11 onto the product spool 30 vacuum orderly arrangement. The second vacuum chamber 21 is connected to a vacuum source through a vacuum port 22.

During operation, both vacuum chambers are first evacuated. Thereafter, a gas is fed through an inlet port 23 in the evacuated first vacuum chamber 13. The gas is drawn into the lumen of the tubing through one or more of the openings 12, and flows through the lumen of the tubing 11 while the latter passes through the tubular reaction conduit 15. The gas is excited to a plasma state by means of a radiofrequency glow discharge as it flows through a radiofrequency (RF) field generated by one or more electrodes 24, which are preferably located exteriorly to the tubular reaction conduits, thereby not exposed to vacuum or to gas in the evacuated apparatus. Residual gas exits the lumen of the tubing through one or more of the openings 12 in the tubing 11 after the tubing enters the evacuated second vacuum chamber 21, then flows to the vacuum source through an outlet port 22. The first vacuum chamber 13 may be independently evacuated through its own connection 25 to a vacuum source, but during the plasma treatment operation, the first vacuum chamber 13 is preferably isolated from the vacuum source by a closed valve 26. Movement of the tubing through the apparatus from a dispenser such as a supply spool to a receiver such as a product spool may be achieved in various ways. In the case of a product spool, the spool may be mechanically rotated, such as by means of a step motor or other drive source (not shown). Alternatively, the tubing may be driven by means of a mechanism that grips and pulls the tubing through the tubular reaction conduit, such as an S-drive roller assembly as disclosed in FIG. 2 of U.S. Pat. 4,692,347, incorporated herein by reference. These and other means of causing the tubing to pass through the tubular reaction conduit will be evident to one knowledgeable in the handling of tubing.

The design in FIG. 1 assumes a co-current flow of the gas with the tubing, but the path of the gas or gas mixture may be either co-current or countercurrent to the direction of movement of the tubing. The direction of the latter can be changed by changing the locations of the gas inlet and the vacuum outlet. Alternatively, it may be changed by exchange of the supply and product spools (and associated drive mechanisms, not shown). Two tubular reaction conduits are depicted in FIG. 1, but any number of such tubular reaction conduits may be employed, suitably connected in parallel to the first and second evacuated chambers. Or, optionally, the apparatus may have only a single tubular reaction conduit, so mounted. The internal diameters of a multiple number of tubular reaction conduits may be identical one to another, or they may be varied one to another whereby more than one size of tubing may be processed concurrently. Ordinarily, either a single RF electrode or a pair of RF electrodes would be used. When a pair of RF electrodes is used such as depicted in FIG. 1, a gas plasma activated by the RF electrodes is localized to the location of the electrodes and particularly to the intervening space between them. This is often preferable in plasma coating processes utilizing a plasma polymerization method. When a pair of RF electrodes is used, one of the electrodes is normally the signal-transmitting electrode and the other electrode is a grounding electrode. When a single RF electrode is used, a somewhat more diffuse plasma zone extending sideways in both directions from the site of the electrode will occur within the tubular reaction conduit.

Figure 2:
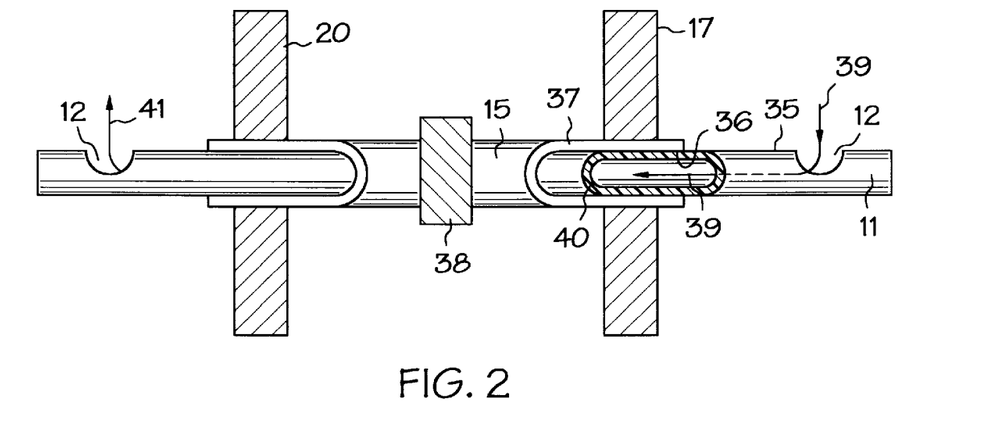
FIG. 2 is a schematic view illustrating gas flow during plasma treatment of the lumen of a perforated tubing.

In FIG. 2, an enlarged view of a tubular reaction conduit is shown, along with a portion of tubing traveling therethrough to be plasma-modified on its interior surface. Cut-away views are provided to clarify the preferred pathway of gas flow through the plasma reactor. A tubular reaction conduit 15 is shown mounted between the base plate 17 of a first evacuated chamber and a base plate 20 of a second evacuated chamber. A length of tubing 11 having openings 12 therein is shown entering one end of the tubular shaped conduit 15 wherein the outer surface 35 of the tubing 11 is in close proximity to the inner surface 36 of the wall 37 of the tubular reaction conduit 15. A zone of gas plasma is generated in the lumen of the tubing by an RF electrode 38. The latter is shown herein as a metallic member encircling the tubular reaction conduit. An arrow 39 indicates the flow of a gas into the lumen of the tubing through an opening 12 in its wall 40, this flow of gas feeding the gas plasma (not shown) in the tubing lumen in the region of the electrode. At the opposite end of the tubular-shaped conduit 15, another arrow 41 shows the direction of flow of residual gas from the plasma zone out through an opening 12 in the tubing 11.

A pressure difference between the two chambers at opposite ends of the tubular reaction conduit provides an impetus for this flow of the gas through the tubing lumen. The outer surface of the tubing is preferably in such close proximity to the inner surface of the tubular reaction conduit as to essentially occlude flow of gas through any annular space yet existing between the tubing and the reaction conduit. Because of this occlusive contact, at least 50%, more preferably at least 70%, of the gas flow between the two evacuated chambers will take place via the tubing lumen. Ideally at least 85% of the gas flow will occur via the tubing lumen. The percentage of gas flow through the lumen of the tubing can be maximized by adjusting the internal diameter of tubular reaction conduit to match as closely as possible the external diameter of the tubing, so as to define as narrow an annulus as possible. In fact, the external surface of the tubing may be in full sliding contact with the internal surface of the conduit, such that no annular space is readily observable. This desirability is to be balanced against the development of frictional resistance to movement of the tubing's outer surface in sliding contact with the inner surface of the tubular reaction conduit. In light of this friction problem, when the internal diameter of the conduit is larger than the external diameter of the tubing to be treated, any gap between the internal surface of the conduit and the external surface of the tubing should not be so large as to support development of a glow discharge under conditions favorable for glow discharge formation in the tubing lumen. Normally, a gap no larger than 2 mm, preferably no larger than 1 mm, will be sufficient to inhibit glow discharge development in the annulus peripheral to the circumference of the tubing.

The periodic interval between the openings sequentially arranged along a continuous length of nonporous or low-porosity tubing may be varied depending upon the tubing lumen size and the plasma treatment desired to be effected. The term "periodical interval" is used herein to describe a regularly repeating interval. Generally, for wider utility of the treated product, the interval (i.e., spacing) between the openings should be as long as conveniently possible. The length of this interval should be balanced against increasing pressure drop with increasing distance of gaseous travel down the tubing lumen between openings. The interval may be increased as a function of increasing internal diameter of the tubing and as a function of decreasing requirement for movement of gas through the lumen. Conversely, the interval should be shorter for tubing of decreased internal diameter and for increased need of movement of gas through the lumen. For tubing with an internal diameter of about 3.5–4 mm, the periodical interval, i.e., the periodic distance between openings, is preferably less than one meter, more preferably less than about 0.8 meter. An interval of about 0.6–0.7 meter (i.e., about 24–28 inches) between openings has been found to be particularly suitable for silicone tubing of such a diameter. In the case of thin-walled, low porosity vascular graft materials, the allowable range of interval length between openings may be considerably larger than for thicker-walled, nonporous tubing suitable for catheter or feeding tube uses.

A much greater movement of a polymerizable gas through the lumen is generally needed in contrast to a suitable rate of movement of a nonpolymerizable gas such as argon or nitrogen. This is due in part to the consumption of the polymerizable gas in the glow zone, and in part to the desire, in accordance with this invention, to deposit crack-free coatings having thicknesses in excess of 1000 Å, preferably even in excess of 5,000 Å. Monomer vapor flow rates to be employed to produce the thicker coatings are preferably in the range of 1–20 sccm per tubing lumen, more preferably 3 to 10 sccm per tubing lumen. Consequently, a significantly large pressure drop is preferably employed between the two vacuum chambers to drive the polymerizable monomer vapor at these desirable flow rates into the glow discharge zone within the tubing lumen. By way of example, at a monomer vapor flow rate of about 5 sccm, a suitable pressure differential through the lumen of tubing of about 3.9 mm lumen diameter, measured across a periodic distance of about 0.71 meter between openings, where the tubing is passing through the tubular reaction conduit and plasma polymerization is in progress, will typically average greater than 30%. Such a minimum pressure differential may be applicable and preferred in the case of a polymerizable monomer such as 1,1,3,3-tetramethyldisiloxane that simultaneously generates a gaseous byproduct (i.e., hydrogen) as a direct consequence of plasma polymerization. In the case of a monomer consumed in the plasma polymerization without any significant generation of a gaseous byproduct, a pressure drop of at least about 50% is preferred, and pressure differentials as great as 95–96% may be advantageously employed.

To achieve such high flow rates of monomer vapor to the glow discharge zone in the tubing lumen, a shorter rather than a longer interval is thus preferred between openings in the tubing in plasma polymerizations. This is especially desirable so as to attain as narrow a range of pressure of monomer vapor as possible entering the glow discharge zone, thereby fostering uniform thickness of a deposit of a plasma polymerizate.

Control of the pressure differential may be achieved in various ways. One approach is to set and maintain the pressure in the vacuum-connected downstream vacuum chamber, and let the monomer-fed upstream vacuum chamber reach an equilibrium pressure level dependent on the monomer vapor feed rate. Another, more preferable, approach is to set and maintain the pressure in the monomer-fed upstream vacuum chamber and let the downstream vacuum chamber pressure seek equilibrium. The latter is preferable in that greater control of monomer vapor pressure entering the tubing opening is thereby exerted. The system pressure may be set and maintained, for example, by connecting a pressure monitor (mounted on the appropriate chamber in accordance with one or the other of the above two approaches) to a controller that controls the setting of a throttle in the vacuum line, thereby to increase or decrease the evacuation rate of the vacuum-connected chamber. For instance, the controller may be an electronic device, and the throttle, a form of butterfly valve, the electronic device opening or closing the butterfly valve in response to a gas pressure signal from the pressure monitor.

The length of the tubular reaction conduit may be generally varied at will. A practical upper limit for the length of the tubular reaction conduit is about 1.5 meters, because of frictional resistance to movement between the inner surface of this conduit and the exterior surface of a tubing being drawn through it. A practical lower limit for the length of the tubular reaction conduit is about 0.15 meter. At such a dimension, sufficient space is provided for mounting a pair of RF electrodes and maintaining a directed glow discharge zone between them, while avoiding grounding interference by metallic components of mountings at either end of the conduit. It appears that a preferred result will be obtained when the length of the conduit is in the range of from one-third to twice the length of the interval between openings in a tubing. More preferably, conduit length is either slightly less than the interval length or slightly less than twice the interval length, particularly when two or more lines of tubing are being simultaneously processed through a like number of conduits mounted in parallel arrangement. When a plurality of tubular reaction conduits are employed, their lengths will normally be the same throughout, particularly when only one size of tubing is being treated. However, variation in the length of the tubular reaction conduits is possible, one to another, and may even be preferable in the case where simultaneous processing of nonequivalent sizes of tubing is practiced.

Where frictional resistance to movement is a significant factor, it may be preferable to shorten the length of the conduit to as low as the 0.15-meter length. Reduction of the frictional resistance to movement may also be achieved by prior treatment of the inner surface of the tubular reaction conduit with a material of low frictional resistance. It is convenient, for instance, to treat this surface with a plasma of tetrafluoroethylene, thereby depositing an adherent coating of a polyfluorocarbon on the inner surface of the tubular reaction conduit, whereby frictional resistance is lowered. Another option is to deposit a polysiloxane coating from plasma polymerization of 1,1,3,3-tetramethyldisiloxane, this also producing a surface with lowered frictional resistance. Operable conditions for plasma polymerization of 1,1,3,3-tetramethyldisiloxane are disclosed in U.S. Pat. No. 4,824,444, incorporated herein by reference.

The tubular reaction conduit is normally selected from materials transparent to RF energy. Optimal materials for this purpose typically include high silica glasses or synthetic quartz. Such materials have the additional advantage of being rigid and unaffected dimensionally by the condition of atmospheric pressure outside and the vacuum pressure inside the conduits. It is also highly desirable to utilize, for tubular reaction conduits, materials that are transparent to visible light, so that one may conveniently observe the development and maintenance of a glow discharge in the tubing lumen. Even in the case of white-pigmented opaque rubber tubing, sufficient translucence is present to indicate the presence of a glow discharge in the tubing lumen, the observance of which is beneficial to the operator in the practice of the invention.

Figure 3A:
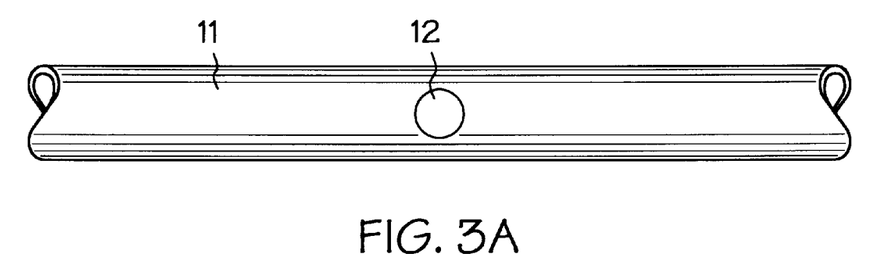
FIG. 3a shows a top view of a perforated length of tubing.
Figure 3B:
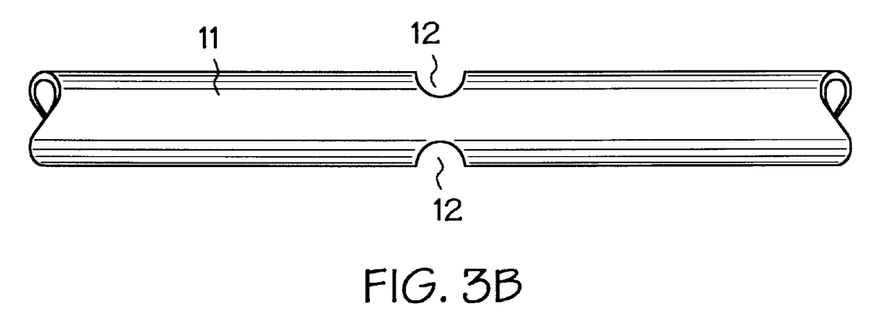
FIG. 3b shows a side view of a perforated length of tubing.

A variety of means for providing periodically spaced openings in the tubing may be advantageously employed. The term opening as used herein can denote either a single aperture (i.e., hole or perforation) or a plurality of apertures grouped together. As one example, FIG. 3 shows a top view (3a) and a side view (3b) of a tubing wherein openings have been placed by a perforating process. In this figure, a tubing 11 is shown as having been punched or perforated through both walls to provide a grouping of two oppositely positioned perforations 12. Apertures may be introduced by punching, drilling, ablating by laser light, or such like. The apertures may be single or multiple in number at each spaced interval site (e.g., a single hole or perforation through the wall, a pair of holes or perforations facing one another punched through opposing hemispheres of the tubing, three holes burned through the tubing wall at 120 degree angles by laser light).

Figure 4A:
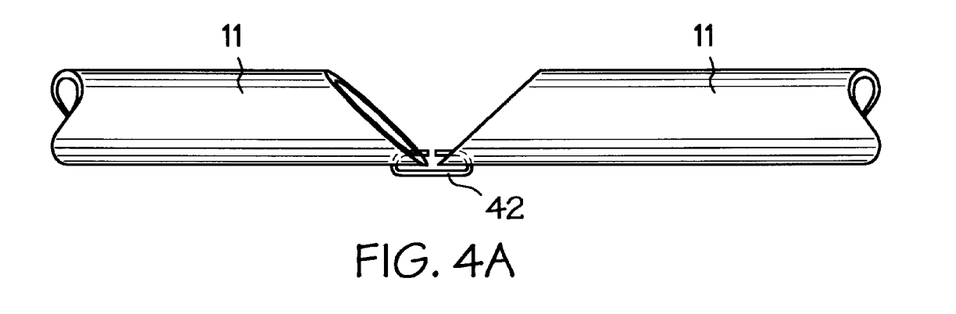
FIG. 4a shows a top view of an end-to-end linkage of pre-cut lengths of tubing.
Figure 4B:
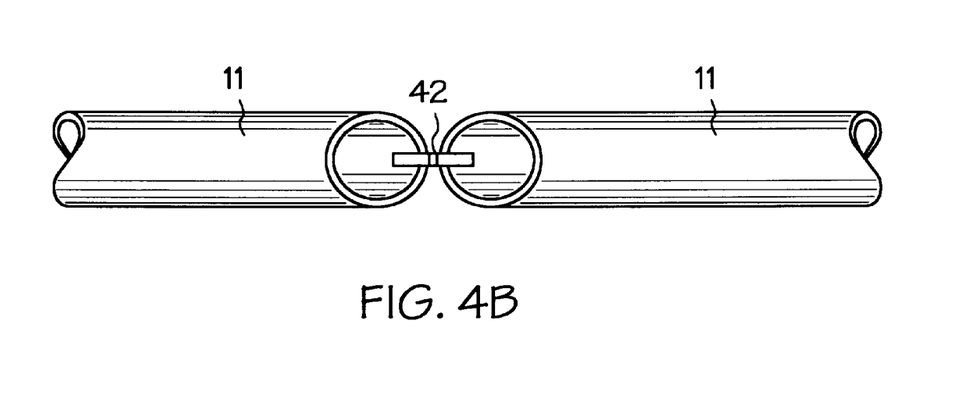
FIG. 4b shows a side view of an end-to-end linkage of pre-cut lengths of tubing.

As an alternative method involving a linear assembly of pre-cut sections, FIG. 4 shows a top view (4a) and a side view (4b) of two end sections of tubing 11 having their ends attached by means of a staple 42. A continuous linear assembly of pre-cut sections of tubing may be constructed by connecting the pre-cut sections with staples, ties, heat-fused bonds, porous connectors, or other such means of connection. The linear assembly made in this manner can serve as an equivalent to a continuous tubing in the plasma treatment process. It is preferable in the assembly of a linear array of pre-cut tubing that such coupling techniques conveniently provide an opening to the tubing's lumen at the site of connection so that openings need not be made elsewhere in the tubing length. The opening thus may constitute a gap between ends of pre-cut sections at the point of connection. However, both openings via gaps and openings via processes such as perforation may be simultaneously employed if desired in providing a continuous linear assembly of tubing sections for gas plasma coating.

The size of the opening, whether constituting a single aperture or a plurality of apertures grouped together, is preferably equivalent in its aggregate cross-section to at least 85% of the diameter of the tubing lumen, more preferably equivalent to at least 100% of the lumen diameter. For example, if two holes are placed at 180 degree intervals around the circumference of the tubing at a particular perforation site, the cross-sectional area of the two holes added together will preferably be at least equal to the cross-sectional area of the lumen of the tubing. When apertures are significantly smaller than the tubing lumen, mean free path considerations relative to gas flow under the high vacuum conditions typically employed in gas plasma treatments may warrant an optimized total cross-sectional area of aperture groupings that is preferably larger than the cross-sectional area of the tubing lumen. While the above relationships and considerations are given as a guide, they are not to be taken as strict limits or requirements. Ultimately, the openings need only be sufficiently sized so that a majority of the flow of gas from the feed port to the vacuum source preferably follows a path through the lumen of the tubing in the zone of plasma activation, and at a rate sufficient to generate the degree of gas plasma surface modification desired. The openings may be oversized relative to the tubing lumen, but such is not necessarily advantageous. If the tubing is composed of a particularly elastic composition, an oversized opening may result in too much stretchiness in the immediate region of the opening, potentially causing cracking of any plasma polymerizate coating deposited in the lumen at that locality.

Tubing suitable for coating or modification of its lumen surface by the process of this invention may be made of virtually any dielectric material, although the process is particularly suitable for flexible dielectric materials. Examples of such materials include, but are not limited to, tubing made of natural rubber, synthetic latex rubber, silicone rubber, polyolefins, polyamides, polyfluorinated compositions and polyvinyl chloride compositions. Knitted or woven tubular materials manufactured from fibers of polymers such as polyethylene terephthalate or polyurethanes, and intended for use as vascular grafts, are also included. Rigid materials such as glass or ceramic tubing may also be coated by this process. For example, such tubing may consist of pre-cut lengths assembled together by flexible couplings having openings provided thereat and fed through the tubular reaction conduit from a dispenser to a receiver, using dispensing and receiving devices other than spooling devices.

The arrangement of the apparatus and the method of using this arrangement as generally depicted in FIG. 1 and in FIG. 2 are believed to be representative of a preferred mode of using this invention, with the added comment that in a commercially attractive mode one may well employ more than two tubular reaction conduits mounted in parallel arrangement to achieve operating efficiencies. Nevertheless, alternate modalities may be more suitable in specific cases and combinations, while remaining within the spirit and scope of the invention. As such an example, in an apparatus having two tubular reaction conduits mounted in parallel, a single continuous length of tubing may be caused to pass through a first tubular reaction conduit in one direction, enter into a chamber connected to a vacuum source, then return through a second tubular reaction conduit moving in the opposite direction. In this example, both the dispenser and receiver for the tubing would be advantageously located in the same evacuated chamber. In this mode, both passes through the tubular reaction conduits can involve deposition of a gas plasma polymerizate on the tubing's lumen surface, with the change in direction of movement of the tubing specifically resulting in a more absolutely uniform deposition of gas plasma polymerizate along its lumen. Monomer vapor may be fed to the chamber wherein the supply and take-up spools are located, and vacuum drawn from the ends of the tubular-shaped reaction conduits distal to this chamber. Or the direction of monomer feed and vacuum withdrawal may be reversed.

Operating conditions for generation of a gas plasma are commonly known or available to one of ordinary skill in the art. Such conditions usually include providing a gas to a glow discharge chamber at pressures of about 0.01 to 2 torr and exciting the gas to a plasma state by means of a radiofrequency discharge power of typically 3 to 150 watts at a frequency of at least about 500 kHz. Typically, an assigned radiofrequency of 13.56 MHz is used for gas plasma operations to avoid radio interference. The term "gas", as used in this description, may include permanent gases such as nitrogen and argon, polymerizable monomer vapors, mixtures of monomer vapors, and mixtures of monomer vapors with permanent gases. The preferred composition of the gas will depend upon the nature of the surface treatment or composition of a plasma polymerizate to be deposited as a coating on the lumen surface of a tubing, which will in turn depend upon the proposed use of the tubing. If the intended modification of the tubing lumen involves purposes of cleaning, crosslinking, radical implantation or generation of reactive groups on the lumen surface by a gas plasma, permanent gases such as helium, argon, nitrogen or oxygen may be employed. If a coating of a plasma polymerizate is to be deposited, a polymerizable monomer vapor or mixture of such vapors may be fed to the apparatus. Polymerizable monomers include silanes such as methoxy and ethoxy alkylsilanes, siloxanes such as tetramethyl and hexamethyl disiloxane, alkanes such as methane and ethane, olefins such as ethylene and propylene, acetylene and its substituted derivatives, substituted vinyl compounds such as acrylic acid and allylamine, halogenated olefins such as tetrafluoroethylene and vinyl chloride, aromatic compounds such as benzene and styrene, cycloaliphatic hydrocarbons such as cyclohexane, cycloaliphatic amines such as 1,2-diamino- and 1,3-diaminocyclohexane, and so forth. Nonpolymerizable gases may be mixed with polymerizable monomers. The variety of polymerizable monomers and coatings derived therefrom in the field of gas plasma polymerizations is particularly described in a book titled *Plasma Polymerization* by H. Yasuda (Academic Press, 1985), which also describes the theory and practice of gas plasma treatment in general.

Control of deposition rate and thickness of coating is typically attained by adjustment of monomer flow rate, linear speed of the tubing through the tubular reaction conduit, degree of localization of the plasma zone inside the tubing lumen, and the power input. Power input may be varied widely within the range of 3 to 150 watts. A preferred range of power input is 10 to 100 watts, more preferably about 20 to about 50 watts. Control of the plasma zone to a specifically localized zone is preferably done by means of a pair of electrodes, one of which is a ground electrode. The spacing between these two electrodes may be varied within a range of from 5 to 200 mm, more preferably from 10 to 100 mm. For tubing with a 3.6 mm internal diameter, a spacing of about 15 to 30 mm between RF electrodes is found to be particularly suitable in plasma polymerizations for deposition of plasma polymerizates on the lumen wall. Residence time in the glow discharge zone, during which the plasma polymer is deposited, is preferably in the range of 1 to 20 seconds, more preferably 3 to 10 seconds.

By the method of this invention, high monomer flow rates may be successfully used to prepare thick plasma polymerizate coatings of greater than 1000 Å thickness on lumen walls of tubing. Further, this can be accomplished in a manner such that the coatings are essentially free of stress cracks, as judged by resistance of the coatings to permeation of dye.

While this invention is not to be bound by the following theory, it is believed that the ability to generate thicker coatings without concomitant development of stress cracking is a direct result of the ability to feed the plasma zone with a high flow rate of monomer vapor due to the shortened distance of movement through the perforated tubing. Such an unexpected outcome is particularly advantageous, since many surfaces are sufficiently rough on a microscale as not to be adequately covered by a barrier layer of less than 1000 Å thickness.

In accordance with the invention herein described, tight, effective barrier layers are deposited from monomer vapor plasmas at W/FM values in the range of $1\times10^7$ J/kg to $1\times10$ J/kg.

Furthermore, by the method disclosed herein, these coatings may be deposited at thicknesses of between 1000 Å and 50,000 Å (0.1 to 5 micrometers), and particularly at thicknesses of between 5,000 and 25,000 Å (0.5 to 2.5 micrometers) without concomitant formation of cracked coatings.

The modification of the lumen surface may be intended to increase it blood compatibility or thromboresistance to blood. Or a plasma polymerizate coating may be deposited with a view to selective attachment of biological substances or cells thereon for biochemical operations. Or a coating may be applied to the tubing lumen to achieve barrier properties to specific gases or liquids or to attachment or attack by microbiological agents. Alternatively, such coatings may be useful as semipermeable membrane layers for molecular separations.

The following examples are provided to illustrate aspects of the application of the method of the invention to both perforated and assembled lengths of tubing.

EXAMPLE 1

Silicone rubber tubing having an I.D. of about 3.9 mm and an O.D. of about 6.6 mm was coated with a gas plasma polymerizate on its lumen surface using an apparatus of the type generally as depicted in FIG. 1. A pair of 60-cm-length conduits of Vycor glass (trademark of Corning Glass) having an O.D. of about 8.9 mm and an I.D. of about 6.8 mm were connected in parallel arrangement to a monomer-fed vacuum chamber, each at one of its two ends, and to a low pressure vacuum chamber, each at its other end. A single electrode connected to an RF signal generator was mounted externally onto the Vycor glass conduits at the approximate midpoints of the conduits, in contact with both conduits. Two linear assemblies of silicone rubber tubing were coated simultaneously. Each consisted of 55 sections of pre-cut, transparent, silicone rubber tubing, each section being about 61 cm long, connected end-to-end by ties of monofilament thread to provide linear assemblies approximately 33 meters in total length. These were unwound from separate spools located in the monomer-fed vacuum chamber, were passed through the glass conduits at a rate of 0.28 cm per second, and were rewound on separate spools in the low pressure vacuum chamber. During passage of tubing through the glass conduits, a plasma glow was maintained within the tubing lumens by means of a 13.56 MHz radiofrequency signal to the electrode at a discharge power of 150 watts. System pressure in the low pressure vacuum chamber was set and maintained at 120 mtorr, while 1,1,3,3-tetramethyldisiloxane monomer vapor was fed to the other vacuum chamber at a feed rate of 21 sccm. A calculation of the W/FM ratio gave $7.2\times10^7$ J/kg. Pressure in the monomer-fed vacuum chamber was initially about 159 mtorr, but rose during plasma polymerization, reaching a final level of 280.8 mtorr. Thus, pressure differential across the tubular reaction conduits was initially about 25%, but rose to 57%. A crosslinked polysiloxane coating was deposited on the surfaces of the lumens.

The uniformity of coverage of the lumen surfaces was subsequently determined by exposing the tubing lumens to a solution of Sudan Red III (Certified Biological Stain, EM Science, N.J.) dissolved in polyethylene glycol (average M.W. 600) at a level of 0.67 g per liter. The dye would absorb into exposed surfaces of the silicone rubber, except where the surface was protected by plasma polymerizate. Six sections were selected from each string of the two plasma-treated silicone tubing assemblies, starting with the fifth section followed by every tenth section thereafter. These were each cut into 12 segments of about 5 cm length, resulting in a total of 144 specimens. Approximately 0.2 ml of dye solution was placed in the midpoint of the lumen of each specimen by means of a syringe, wetting about half of the interior surface of the segment with dye solution. The lumen surfaces were left in contact with the dye solution for two hours. The specimens were thoroughly washed with water thereafter, then visually examined for red dye penetration. No dye staining was evident in 137 of the specimens, showing the uniformity of the plasma coating process. Of the seven specimens showing dye uptake, six were segments at the very ends of the 61-cm long sections, and were believed to be caused by cracking of polymerizate deposits due to stretching effects on the tubing from friction during processing.

EXAMPLE 2

Silicone rubber tubing of the same type as in Example 1, but consisting of approximately a 12-meter continuous length, had 6.4-mm holes mechanically punched into it at 61 cm intervals, there being a pair of such holes oppositely juxtaposed at each perforation site. The lumen of the tubing was coated with a gas plasma polymerizate in the same manner as in Example 1, using a single Vycor glass conduit. The second Vycor glass conduit was filled with a stationary piece of the same type of tubing to equalize gas flow through the two tubular reaction conduits. The interior surfaces of the Vycor glass conduits were preexposed to a gas plasma of tetrafluoroethylene to deposit a fluorocarbon coating thereon for lowered frictional resistance. Two electrodes were used, these being placed in sequence in exterior contact with the conduits, with a gap of 2.5 cm between the electrodes. The electrode in the downstream position was the ground electrode. System pressure in the low pressure vacuum chamber was set and maintained at 20 mtorr. Feed rate of tetrafluoroethylene monomer was 9.9 sccm and RF discharge power was 70 watts at 13.56 MHz. Calculated W/FM ratio was $9.5 \times 10^7$ J/kg. Pressure in the monomer-fed vacuum chamber was initially at 411.2 mtorr upon addition of tetrafluoroethylene monomer vapor, but rose to greater than 500 mtorr during plasma polymerization. Pressure differential across the tubular reaction conduit was thus in the range of 95–96%. The lumen of the silicone rubber tubing was coated with a fluorocarbon plasma polymerizate. Three 61-cm sections were excised from the coated tubing. These were cut into segments about 5 cm long for a total of 36 specimens, and were examined in dye tests as described in Example 1. No dye staining was evident in 35 of the 36 specimens, showing the uniformity of coating achieved by this method.

EXAMPLE 3

Using the method and apparatus as in Example 2, a white-pigmented silicone rubber tubing having an I.D. of about 3.9 mm and an O.D. of about 6.75 mm was coated on its lumen surface with a gas plasma polymerizate of allyl amine. The tubing consisted of four 61-cm sections connected together into a linear assembly by monofilament thread ties, and having additionally attached to one end a 61-cm lead section and to the other end a 61-cm trailing section for handling purposes between spools. Monomer feed rate was 3.57 sccm and the electrode discharge power was 100 watts with a pulse mode (475 microsec on/ 525 microsec off). System pressures were approximately 521 mtorr in the monomer-fed chamber and 50 mtorr in the vacuum-connected chamber, corresponding to a pressure differential of 90%. The four 61-cm sections were each cut into 12 two-inch segments after having been coated on their lumen surfaces. These were examined in a dye test for uptake of Bromthymol Blue (negatively charged dye, EM Science, N.J.) by the weakly cationic allylamine plasma polymerizate. Approximately 0.2 ml of aqueous dye solution consisting of 0.8 g of Bromthymol Blue per liter of water was placed within the lumen of each specimen. After two hours of exposure, the dye solution was thoroughly washed out, and the specimens were sliced in half in their long direction and visually examined. All 48 specimens showed a visually uniform uptake of Bromthymol Blue dye, demonstrating the uniformity of the coating process.

EXAMPLE 4

Using the same procedure as is in Example 2, a white-pigmented opaque silicone rubber tubing having an I.D. of about 3.9 mm and an O.D. of about 6.75 mm was coated with a plasma polymerizate from tetrafluoroethylene on its lumen surface. The tubing consisted of 25 sections 61 cm in length connected by monofilament ties into a linear assembly, with a total length of approximately 15 meters. Uniformity of the fluorocarbon coating on the tubing lumen was examined by the Red Sudan III dye method as before, except that the specimens, being opaque, were sliced in half longitudinally for visual examination after dye exposure. The plasma polymerizate coating was found to be uniform throughout the tubing length.

EXAMPLE 5

White-pigmented opaque silicone rubber tubing having an I.D. of about 3.9 mm and an O.D. of about 6.75 mm was coated with a gas plasma polymerizate on its lumen surface using an apparatus of the type generally as depicted in FIG. 1, but having four parallel 25-cm long tubular reaction conduits made of Vycor glass having an O.D. of about 8.9 mm and an I.D. of about 6.8 mm. A pair of electrodes were mounted exteriorly at the approximate midpoints of the glass conduits, in contact with all four conduits, and having a spacing between the electrode pair of 2.5 cm. Four linear tubing assemblies, each of which consisted of 15 sections of pre-cut silicone rubber tubing sections 61 cm long connected end-to-end by tying with monofilament thread, were unwound from separate spools located in the monomer-fed vacuum chamber, were passed through the glass conduits at a rate of 0.25 cm per second, and were rewound on separate spools in the low pressure vacuum chamber. Tetrafluoroethylene was fed as monomer to a first vacuum chamber at a rate of 20 sccm, and system pressure in the monomer-fed vacuum chamber was set and maintained in the range of 660–700 mtorr. A vacuum was drawn on the system through the second chamber. Pressure in the second vacuum chamber was in the range of 215 to 340 mtorr during plasma coating, with a corresponding average pressure differential of about 57%. During passage of the tubing through the conduits, a plasma glow was maintained within the tubing lumens by means of a 13.56 MHz radiofrequency signal operating at a discharge power of 50 watts. W/FM was calculated to be $3.4 \times 10^7$ J/kg. Four of the sections were examined for uniformity of coverage of the lumen surfaces as in Example 4. No dye staining was evident in the specimens, showing the uniformity of the plasma coating process.

EXAMPLE 6

White-pigmented opaque silicone rubber tubing of the same type as in Example 5, but consisting of four parallel lengths of continuous, perforated tubing, each about 19 meters long, was coated with a gas plasma polymerizate of tetrafluoroethylene on its lumen surface in the same manner as in Example 5. The openings were spaced periodically at about a 71 cm distance. Tubing draw rate was 0.25 cm per second. Tetrafluoroethylene monomer feed rate was 20 sccm, and system pressure in the monomer-fed vacuum chamber was set and maintained in the range of 680–700 mtorr. A vacuum was drawn on the system through the second chamber. Pressure in the second vacuum chamber averaged 183 mtorr during plasma coating, which corresponded to a pressure differential of about 73%. The RF plasma glow was maintained at a discharge power of 40 watts. The calculated W/FM ratio was $2.6 \times 10^7$ J/kg. Sections were subsequently examined for uniformity of coverage of the lumen surfaces as in Example 4. No dye staining is evident in the specimens, showing the uniformity of the plasma coating process.

A 71-cm section between openings was excised from the coated tubing prepared in Example 6, and its lumen surface was examined by ESCA (electron spectroscopy for chemical analysis). Five areas were examined by ESCA corresponding to positions at approximately 11, 22, 35.5, 49, and 60 cm intervals from the monomer inlet opening of the section. Data were acquired using monochromated Al x-rays, and analysis areas were 1.1 mm in diameter. Atomic concentrations at the different locations are listed in Table 1. The five areas were all elementally quite similar. The F/C ratio equalled or was close to the theoretical value of 2.0 in four of the five positions assayed by ESCA.

The above description, drawings and examples of the invention have been given by way of illustration of what is believed to be the best embodiment. Obviously, the invention may be embodied in other derivations and variations without departing from the spirit and the scope of the invention as described herein, and in the claims that follow.

TABLE 1

| ESCA atomic concentrations | Carbon | Oxygen | Fluorine | Silicon | Nitrogen | F/C ratio |
| --- | --- | --- | --- | --- | --- | --- |
| position: | | | | | | |
| 11 cm | 36.0 | 2.3 | 60.8 | 0.8 | 0.1 | 1.69 |
| 22 cm | 34.4 | 1.1 | 64.3 | 0.3 | nd | 1.87 |
| 35.5 cm | 33.7 | 0.7 | 65.5 | 0.2 | nd | 1.94 |
| 49 cm | 33.9 | 1.8 | 63.0 | 1.2 | nd | 1.86 |
| 60 cm | 33.1 | 0.5 | 66.3 | 0.1 | nd | 2.00 | nd: not detected.

I claim:

1. An article comprising a continuous length of a tubing having an external surface and an internal surface, the internal surface defining a continuous lumen, the tubing having a plurality of openings or groups of openings sequentially arranged at a periodic interval along its length by which fluid communication is established between the external surface and the internal surface, each opening or group of openings having an aggregate cross-sectional area equal to at least 85% of the lumen's cross-sectional area, the internal surface being coated with a coating of a plasma polymerizate deposited from a glow discharge gas plasma, the coating being essentially free of stress cracks and having a thickness greater than 1000 Å.

2. The article of claim 1 wherein the coating of the plasma polymerizate has been deposited from the glow discharge gas plasma at a power input ratio W/FM of between $1 \times 10^7$ J/kg and $1 \times 10^8$ J/kg.

3. The article of claim 2 wherein a monomer vapor comprising an olefinic compound is fed to the glow discharge gas plasma.

4. The article of claim 2 wherein a monomer vapor comprising a siloxane compound is fed to the glow discharge gas plasma.

5. The article of claim 3 wherein the olefinic compound is tetrafluoroethylene.

6. The article of claim 4 wherein the siloxane monomer is 1,1,3,3-tetramethyldisiloxane.

7. The article of claim 2 wherein the external surface is essentially free of the coating of plasma polymerizate.

8. The article of claim 5 wherein the plasma polymerizate has a thickness of between 5,000 and 25,000 Å.

9. The article of claim 8 wherein the tubing comprises a silicone rubber tubing.

10. The article of claim 1 wherein a continuous linear assembly of pre-cut tubing sections is substituted in place of the continuous length of tubing.

11. The article of claim 10 wherein the coating of the plasma polymerizate has been deposited from the glow discharge gas plasma at a power input ratio W/FM of between $1 \times 10^7$ J/kg and $1 \times 10^8$ J/kg.

12. The article of claim 11 wherein the coating comprises a plasma polymerizate of tetrafluoroethylene and the tubing comprises a silicone rubber tubing.

13. The article of claim 2 prepared by passing the continuous length of the tubing through an evacuated tubular reaction conduit having a proximal end and a distal end, simultaneously passing a monomer vapor through the lumen of the tubing, and exciting the monomer vapor to a glow discharge gas plasma by means of a radiofrequency signal transmitted from an electrode mounted externally to the tubular reaction conduit, the monomer vapor entering the lumen of the tubing via at least one of the openings from a source of monomer vapor located exteriorly to the tubing at a site adjacent to the proximal end of the conduit, the monomer flowing toward a vacuum source located exteriorly to the tubing at a site adjacent to the distal end of the conduit, at least 50% of monomer vapor flowing toward the vacuum source being passed by way of the lumen of the tubing during passage of the tubing through the reaction conduit.

14. A medical device comprising a section of any length cut from the article of claim 2.

15. A medical device comprising a section of any length cut from the article of claim 12.

* * * * *